US00PP35412P3

(12) United States Plant Patent
Zhang et al.

(10) Patent No.: US PP35,412 P3
(45) Date of Patent: Oct. 3, 2023

(54) HEMP PLANT NAMED 'CAF#13/2020'

(50) Latin Name: *Cannabis sativa*
Varietal Denomination: CAF#13/2020

(71) Applicant: Creston Aquaponic Spring Farm Inc., Richmond (CA)

(72) Inventors: Ping Zhang, Richmond (CA); Miguel Gallach Caballero, Vienna (AT); Javier Gallach Caballero, Vienna (AT)

(73) Assignee: Creston Aquaponic Spring Farm Inc.

( * ) Notice: Subject to any disclaimer, the term of this patent is extended or adjusted under 35 U.S.C. 154(b) by 0 days.

(21) Appl. No.: 17/300,106

(22) Filed: Mar. 9, 2021

(65) Prior Publication Data

US 2023/0060124 P1 Feb. 23, 2023

(51) Int. Cl.
*A01H 6/28* (2018.01)
*A01H 5/02* (2018.01)

(52) U.S. Cl.
USPC ..... Plt./258
CPC ..... *A01H 6/28* (2018.05)

(58) Field of Classification Search
USPC ..... Plt./258
See application file for complete search history.

(56) References Cited

U.S. PATENT DOCUMENTS

PP33,182 P3 * 6/2021 Klettke ..... Plt./258
PP34,724 P2 * 11/2022 Azwell ..... Plt./258
PP34,828 P2 * 12/2022 Adams ..... Plt./258

OTHER PUBLICATIONS

UPOV Test Guidelines for *Cannabis sativa*. 2012. Internation Union for the Protection of New Varieties of Plants. https://www.upov.int/edocs/tgdocs/en/tg276.pdf. 29 pgs. (Year: 2012).*

* cited by examiner

*Primary Examiner* — Karen M Redden
(74) *Attorney, Agent, or Firm* — Michelle Bos Legal LLC

(57) ABSTRACT

A vegetatively reproduced hemp (*Cannabis sativa* spp.) cultivar named 'CAF#13/2020' notable for its high cannabidiol (CBD) content, low Δ9-tetrahydrocannabinol (THC) content, and adaptation to growing conditions in Canada and the northern United States.

2 Drawing Sheets

Latin name: *Cannabis sativa*.
Variety denomination: 'CAF#13/2020'.

BACKGROUND OF THE VARIETY

*Cannabis sativa* spp. is an annual herbaceous dioecious species, indigenous to the Himalayan Mountains, Central Asia and the Indian subcontinent, and now found worldwide as a result of widespread cultivation. *Cannabis sativa* spp. has been historically used for a variety of purposes, such as industrial fiber, seed, oil, recreation, food, religious mood and medicine.

The *Cannabis sativa* spp. is legally divided into two types, which are defined by the content of $\Delta^9$-tetrahydrocannabinol (THC) in the flowers. The species is called "hemp" when the content of THC is below 0.3% in dry weight; it is called "marijuana" when the THC content is over 0.3% in dry weight.

The growth of the market for cannabidiol (CBD) derived from *Cannabis sativa* spp. has been significant in recent years, and it is expected to increase. Consequently, there is a high demand in the marketplace for *Cannabis sativa* spp. varieties with high CBD content and low THC content.

The new hemp plant 'CAF#13/2020' was developed in the course of a breeding program carried out by the inventors at Richmond, British Columbia, Canada. The inventors developed a base population of *Cannabis sativa* plants comprising a pool of hundreds of plants grown from seeds obtained after two generations of random mating, beginning in 2019, between about two dozen hemp varieties owned by the company. The base population then underwent two rounds of selection (with selection intensity 10%), and dozens of randomly chosen plants were selected for a final round of phenotyping. 'CAF#13/2020' showed the highest CBD yield (7.380%) in dry flower while having a THC concentration of less than 0.3% (0.277%) by weight. 'CAF#13/2020' was first asexually reproduced in 2019 at Richmond, British Columbia, Canada via micro-propagation, and has been observed to remain true to type over successive asexually propagated generations.

BRIEF DESCRIPTION OF THE VARIETY

'CAF#13/2020' is a vegetatively reproduced hemp (*Cannabis sativa* spp.) cultivar distinguished from other commercially produced hemp varieties by its high CBD content, low THC content, and adaptation to growing conditions in Canada and the northern United States. It is also identifiable by its unique genotype, defined by 845,500 single nucleotide polymorphisms detected against the representative reference genome cs10 (GenBank: GCA_900626175.2; RefSeq: GCF_900626175.2) at the National Center for Biotechnology Information (NCBI).

'CAF#13/2020' is distinguished from other known varieties by its relatively high CBD content and low THC content. The claimed variety, the parentage of which is unknown, compares favorably to other low-THC hemp varieties evaluated by the inventors. Table 1 below shows a comparison of the claimed variety to 20 other hemp varieties, selected from among the top 10% of the better strains produced in the inventor's breeding program. The comparison varieties represent those with the most favorable analytical values and morphology as determined by the breeding program goals.

TABLE 1

Comparison of 'CAF#13/2020' to Other Known Hemp Varieties

| Sample # | CBD (CBD + CBDA) | THC (THC + THCA) |
|---|---|---|
| 1 | 2.97 | 0.191 |
| 2 | 4.66 | 0.206 |
| 3 | 5.90 | 0.232 |
| 4 | 9.54 | 0.326 |
| 5 | 8.27 | 0.355 |
| 6 | 6.62 | 0.297 |
| 7 | 4.09 | 0.195 |
| 8 | 4.15 | 0.219 |
| 9 | 5.90 | 0.227 |
| 10 | 8.69 | 0.364 |
| 11 | 4.15 | 0.178 |
| 12 | 9.34 | 0.355 |
| CAF#13/2020 | 7.38 | 0.277 |
| 14 | 3.17 | 0.164 |
| 15 | 7.56 | 0.312 |
| 16 | 7.94 | 0.367 |
| 17 | 6.60 | 0.257 |
| 18 | 4.91 | 0.233 |
| 19 | 4.66 | 0.168 |
| 20 | 4.11 | 0.198 |

Table 2 below shows a comparison of the claimed variety to hemp plant 'Painted Lady' (U.S. Plant Pat. No. 33,182).

TABLE 2

Comparison of 'CAF#13/2020' to Hemp Plant 'Painted Lady'

| | 'CAF#13/2020' | 'Painted Lady' |
|---|---|---|
| Stem color | Yellow-green 144A to 146A, with white 156A to 156D on woody parts | Green 128A to N134C, with red and purple striping on woody parts |
| Leaf color | Yellow-green 147C, green NN137D and yellow-green 147B | Green 134B |
| Petiole color | Yellow-green 144A | Green 134C |

DETAILED BOTANICAL DESCRIPTION OF THE VARIETY

Figure 1:
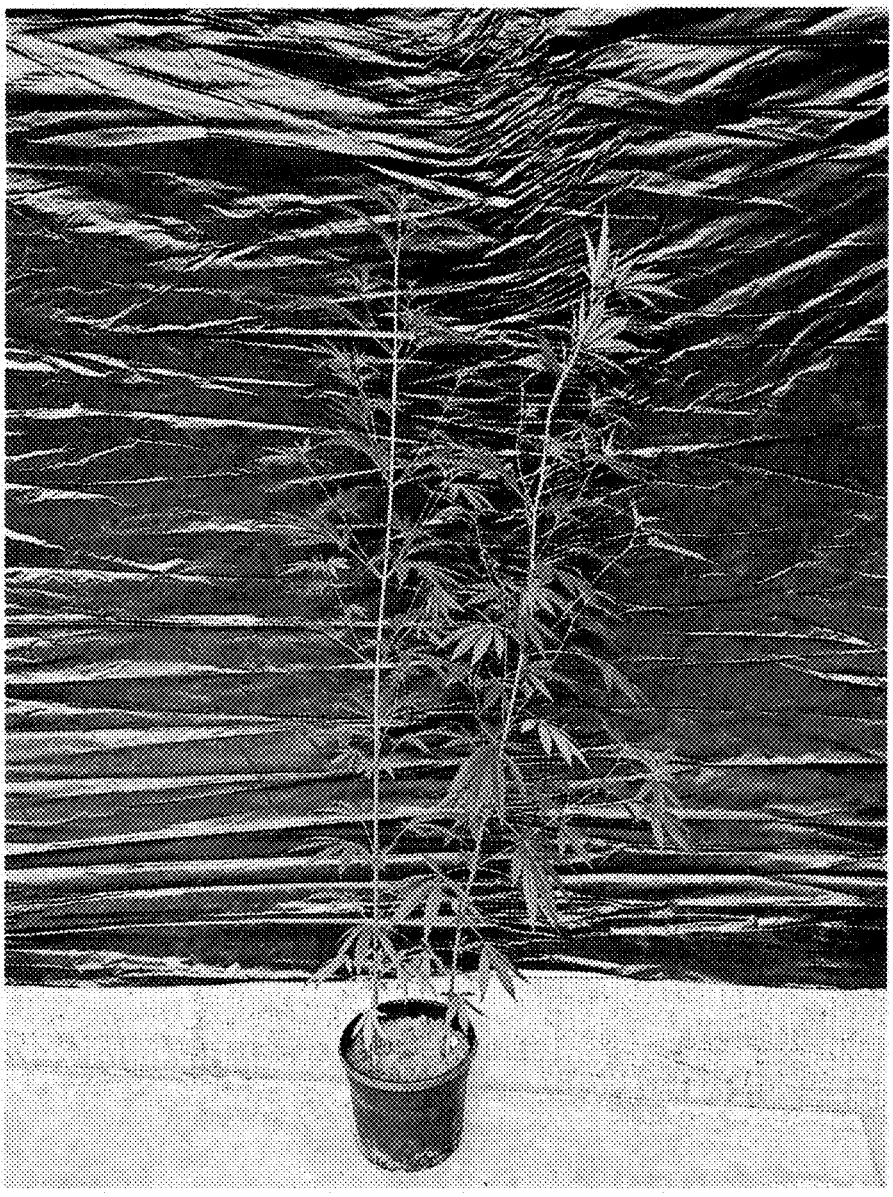
FIG. 1 is a photograph showing the claimed hemp plant.
Figure 2:
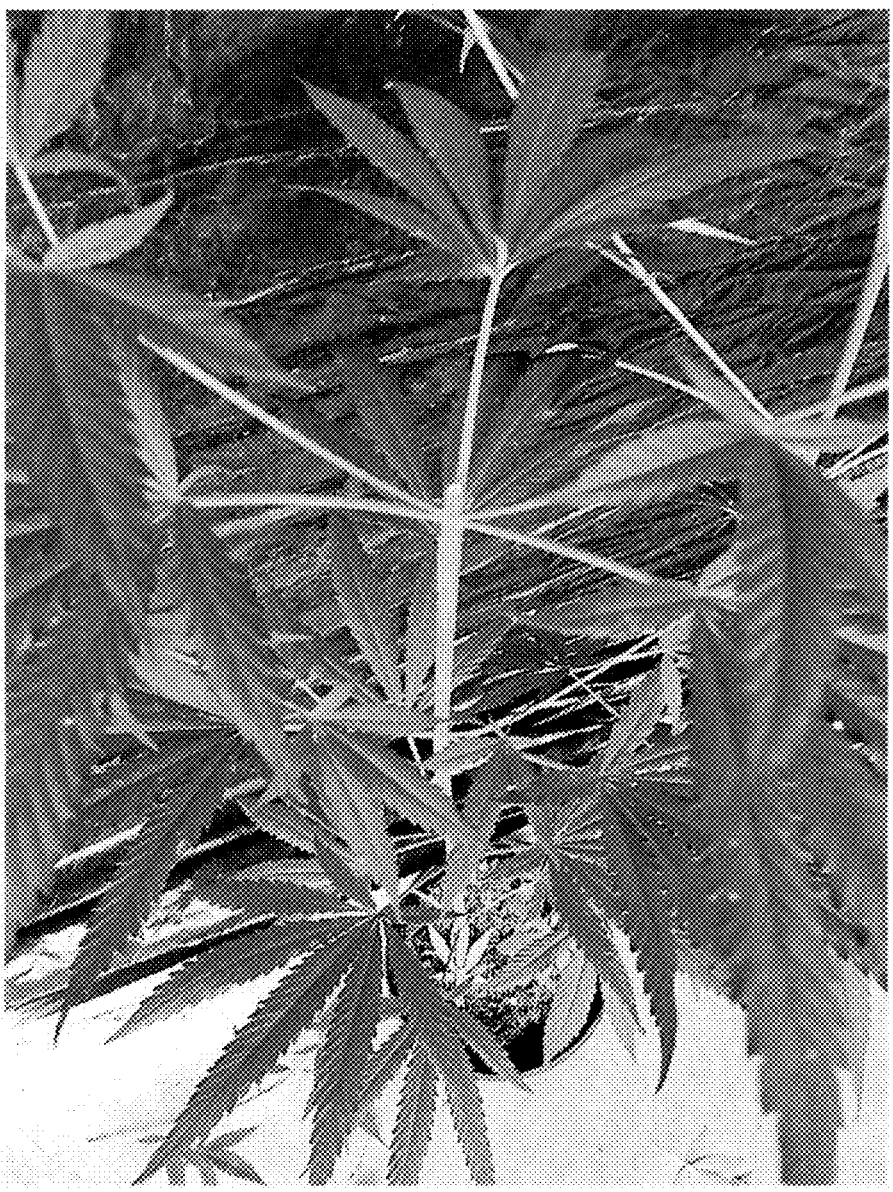
FIG. 2 is a photograph showing the leaves and stalk of the claimed hemp plant.

The patent laws of the United States require that a description for a plant patent be complete and must distinguish the claimed variety. The inventors have sequenced the entirety of the nuclear genome of the 'CAF#13/2020' hemp plant, which provides a genotype of the variety at the nucleotide level.

The following methodology was used:

1. Genomic DNA (gDNA) was extracted from leaf material of 'CAF#13/2020' hemp plants.
2. A DNA-Seq library was prepared for 150 paired-end sequencing with an Illumina NovaSeq 6000 system.
3. Sequenced reads were checked for quality, and high quality reads were mapped to *Cannabis sativa* cs10, the representative genome for this species in the National Center for Biotechnology Information (NCBI). The RefSeq assembly accession is GCF_900626175.2 and the assembled genome was downloaded on Dec. 12, 2020.
4. The reads mapping at each nucleotide position were compiled and the corresponding nucleotides were annotated. If a nucleotide position in 'CAF#13/2020' had a different nucleotide than that of the reference genome cs10, a single nucleotide variant (SNP) was declared.
5. After applying quality filters to avoid false SNPs, the inventors compiled all SNPs located in genic regions and used to genotype 'CAF#13/2020'. We found 845,500 high quality SNPs located in genic regions that can be used as a barcode or unique identifier for 'CAF#13/2020'. The list of these SNPs is compiled in a .bed format file called "CAF#13/2020_genotype.bed".

This application is accompanied by a compact disc containing the file "CAF#13/2020_genotype.bed" in a compressed format (bed.gz) as a unique identifier for the 'CAF#13/2020' hemp plant. Table 2 provides an example of the .bed format:

TABLE 2

Sequence Example

| Line | Column 1 | Column 2 | Column 3 | Column 4 | Column 5 | Column 6 | Column 7 |
|---|---|---|---|---|---|---|---|
| 1 | NC_044371.1 | 40280 | 40280 | A | G | 91 | 0/1 |
| 2 | NC_044371.1 | 40953 | 40953 | G | A | 129 | 1/1 |
| 3 | NC_044371.1 | 245388 | 245388 | A | T, C | 24 | 1/2 |

Referring to Line 1 of Table 2 above, Column 1 ("NC_044371.1") denotes the chromosome; Column 2 and Column 3 ("40280" and "40280") identify the start and end chromosome coordinates of the SNP (which, in the case of SNPs, are equal); Column 4 ("A") identifies the nucleotide in the cs10 reference genome; Column 5 ("G") identifies the alternative nucleotide found in 'CAF#13/2020'; Column 6 ("91") identifies the number of reads mapping at that position; and, Column 7 ("0/1") the called genotype. The allele values of the genotype are 0 for the cs10 reference allele ("A") and 1 for the alternative allele ("G"). Thus, the genotype of 'CAF#13/2020' at position 40280 of chromosome NC_044371.1 is 0/1 or A/G (i.e., it is heterozygous). By comparison, it can be seen at Line 2 of Table 2 that the genotype of 'CAF#13/2020' at position 40953 of chromosome NC_044371.1 is 1/1 or A/A (i.e., it is homozygous for the alternative allele). Finally, there are some cases, such as the example shown in Line 3 of Table 2, where 'CAF#13/2020' has two alternative alleles ("T,C") and the genotype is heterozygous. Homozygous sites in 'CAF#13/2020' for the cs10 reference allele are not included in the file. The submitted file includes 605,723 sites with genotype 0/1, 237,831 sites with genotype 1/1 and 1,946 sites with genotype 1/2.

The complete genotype description provided in the accompanying electronic file precisely defines the claimed variety and distinguishes it from other known hemp varieties.

Potency analysis of 'CAF#13/2020' was performed using test method CR-TM-161 and instrument ID and AIN HPLC CR269-CR274. The analysis confirmed THC concentration of 0.277% by weight, and CBD concentration of 7.380% by weight.

The following detailed description of the claimed plant is provided to further describe the variety. The description is based on observations made at Richmond, British Columbia, Canada. Described plants were grown indoors. All colors are described according to The R.H.S. Colour Chart (Royal Horticultural Society, 6th ed. 2015). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

General characteristics: CAF#13/2020 is a dioecious annual plant that grows upright and exhibits high vigor, especially during the late vegetative stage prior to flowering. The plant has no monecious tendencies without stress manipulation, such as chemical or temperature stress.

*Mature height.*—1.4 to 2.0 meters when grown indoors in a deep pot. Mature height may vary depending on growth conditions.

*Time to harvest:* 90 days to 115 days.

Leaves:

*Phyllotaxy.*—Dependent on growth conditions; mostly alternate with short internodes during early vegetative growth stages after cloning; Sometimes opposite (seedling vegetative stage) and whorled (flowering stage).

*Leaf shape.*—Palmate.

*Number of leaflets.*—3 to 5 in immature plants; as many as 9 at maturity.

*Leaf structure.*—Serrated margins, lightly acicular to lanceolate leaflets, tapering to an acuminate apex; leaf margins jaggedly serrate with each tooth apex angled toward leaflet apex; the apical side of tooth is concave and basal side of tooth is convex.

*Pubescence.*—Leaf hairs are absent.

*Leaf length.*—12 cm to 24 cm.

*Leaf color.*—Yellow-green 147C before flowering stage; Green NN137D and yellow-green 147B during flowering stage.

*Middle leaflet size (largest).*—Length 8 cm to 16 cm; width 1.2 cm to 2.0 cm.

*Middle leaflet length/width ratio.*—4:1 to 8:1.

*Middle leaflet number of teeth.*—19 to 29.

*Secondary veins.*—Percurrent; branched alternately from midvein; grow to tooth apex; color green 143C.

*Petiole length.*—4.2 cm to 8.0 cm at maturity.

*Petiole color.*—Yellow-green 144A; during flowering stage, anthocyanin pigmentation on petioles of fan leaves intensifies and covers both adaxial and abaxial surfaces; darker adaxial surfaces remain red-purple 59A to greyed-purple 187A, but abaxial surfaces are lighter and less densely colored with a range of coloration greyed-purple 184A to greyed-red 180A to greyed-red 178A and 178B and greyed-orange 176A.

*Stipule.*—Length 0.3 cm to 0.9 cm at maturity; width up to 1.2 cm, tapering spinose tip with a wider base about 1.0 mm thick, sometimes curvaceous growth; color varies from green 143A to light 4D on edges.

Stem: Immature axillary branches and immature stem are slightly squared, finely pubescent and longitudinally furrowed in conjunction with the slightly square shape. In later vegetative stages, the stem is generally rounded in appearance with slight furrowing on more recent stem growth. Stem shape is rounded at maturity. Older growth is fuller with lower parts of main stem and oldest branches with slightly woody appearance and outer texture.

*Base stem diameter.*—1.5 cm to 4 cm, depending on nature of initial cutting material.

*Stem color.*—Yellow-green 144A to 146A at vegetative maturity and during flowering; woody lower portions of stem greyed-white 156A to 156D.

*Stem pith type.*—Dependent on plant age, maturity of stem, and initial cutting material.

Inflorescence (female/pistillate flowers): CAF#13/2020 produces pistillate flowers in axils at nodal points along main axis and lateral branches for most of the vegetative growth period. As flowering begins to develop, these start to become more prolific clusters of individual flowers that appear on increasing branching growth from axillary buds emerging from increasingly short internodes on both the main and lateral axes.

*Proportion of female plants.*—100% of the tested clones.

*Number of flowers per plant.*—Hundreds.

*Flower shape.*—Bilaterally symmetric with overall compressed ovaloid appearance.

*Flower type.*—Apetalous pistillate flowers.

*Flower size.*—Inflorescence 2.5 cm to 10 cm diameter; individual pistillate flowers 5 mm to 12 mm.

*Corolla.*—No defined corolla.

*Bracts.*—Trichomated leaflets with tips emergent from dense floral clusters; Leaflets number 3 or 5 with many bracts having 5 leaflets.

*Bract length.*—Range from 2 mm to 7 mm, sometimes more depending on maturity of flowering spike.

*Bract color.*—Green 139A to lighter yellow-green 147A at base of leaflets.

*Bracteole.*—Short, scale-like, membranous piece of tissue, subtending the underside of pistillate flowers; Similar to stipules but wider, shorter, and buried within the densely clustered pistillate inflorescences; not immediately observable without dissection; color green 141C, with pale thin papery margins yellow 4D, 8D and 11D.

*Calyx shape.*—Membranous, broadly ovate, beaked at the tip, persistent, enclosing the fresh and dry fruit, highly trichomated.

*Calyx color.*—Green NN137B through 143A-143C and yellow-green 144B, N144C, 145A to 145D, and green-white 157A to 157D.

*Stigma.*—Short apical style with two long filiform stigmatic branches; length 4 mm to 11 mm; color yellow 1C to 1D, 2D and 4C, some yellow-green 144C to 145A; When senesced greyed-orange 165A, 165B, 164A; At flower maturity, pistils senesce to reddish-brown.

*Staminate flower.*—Does not exist naturally, only under induced masculinization.

*Trichome shape.*—Capitate stalked glandular multiseriate/uniseriate trichomes, especially on flowering inflorescences and perigonial bracts; capitate sessile glandular trichomes on stems, leaves, and bracts; cystolithic non-glandular cystolithic non-glandular trichomes on leaves.

*Trichome color*.—Yellow 4D and white 155A and NN155A to NN155D; creamy color of varying saturation.

*Terminal bud shape*.—Naked, vegetative, and mixed depending on life stage (vegetative or flowering).

*Terminal bud color*.—Green NN137B through 143A to 143C, yellow-green 144B, N144C, 145A through 145D, and green-white 157A through 157D.

*Emergent bract leaflets color*.—Yellow-green 147A.

*Freshly emergent stigmas, tips and papillae color*.—Yellow 1C through 1D, 2D and 4C.

The cultivar has not been tested for resistance to common viruses and fungal diseases pests or diseases.

The invention claimed is:

1. A new and distinct hemp plant named 'CAF#13/2020' substantially as described herein.

* * * * *